(12) United States Patent
Sciocchetti et al.

(10) Patent No.: US 7,665,345 B2
(45) Date of Patent: Feb. 23, 2010

(54) GASEOUS PRODUCT DETECTING DEVICE

(75) Inventors: Giuliano Sciocchetti, Rome (IT); Massimo Pagliari, Rome (IT); Elvio Soldano, Cesano (IT)

(73) Assignee: Giuliano Sciocchetti, Rome (IT)

( * ) Notice: Subject to any disclaimer, the term of this patent is extended or adjusted under 35 U.S.C. 154(b) by 466 days.

(21) Appl. No.: 10/530,626

(22) PCT Filed: Oct. 8, 2003

(86) PCT No.: PCT/IT03/00608

§ 371 (c)(1),
(2), (4) Date: Dec. 30, 2005

(87) PCT Pub. No.: WO2004/034085

PCT Pub. Date: Apr. 22, 2004

(65) Prior Publication Data

US 2006/0123886 A1 Jun. 15, 2006

(30) Foreign Application Priority Data

Oct. 8, 2002 (IT) .......................... TO2002A0868

(51) Int. Cl.
*G01N 7/00* (2006.01)
(52) U.S. Cl. .................... 73/31.05; 73/31.01; 73/31.02; 73/31.03
(58) Field of Classification Search ................ 73/23.34, 73/31.01, 31.02, 31.03, 31.05
See application file for complete search history.

(56) References Cited

U.S. PATENT DOCUMENTS

| 2,802,132 A | | 9/1957 | Kuhns |
| 4,059,406 A | * | 11/1977 | Fleet .......................... 205/786 |
| 4,297,871 A | | 11/1981 | Wright |
| 4,770,027 A | * | 9/1988 | Ehara et al. ................ 73/23.34 |
| 4,976,135 A | | 12/1990 | Stock |
| 6,006,583 A | | 12/1999 | Hayashi |

* cited by examiner

*Primary Examiner*—Daniel S Larkin
(74) *Attorney, Agent, or Firm*—Ferdinand M Romano, Esq.; Beusse, Wolter, Sanks, Mora & Maire, P.A.

(57) ABSTRACT

A gaseous product detecting device (1; 20; 30; 40; 70) has a measuring cell (6; 59; 60), a filtering element (3; 45) for retaining particulate present in the air entering the measuring cell (6; 59; 60), and a detecting element (13; 50, 56) housed inside the measuring cell (6; 59, 60). A wall (9; 49, 61; 79, 82) of the measuring cell (6; 59, 60) is movable in fluidtight manner between a withdrawn position, in which the measuring cell (6; 59, 60) has a maximum volume, and a forward position, in which the measuring cell (6; 59, 60) has a minimum volume and the detecting element (13; 50, 56) is prevented from being impressed by resting against a shutter surface (5a; 43a, 49b; 82a) of the measuring cell (6; 59, 60).

12 Claims, 4 Drawing Sheets

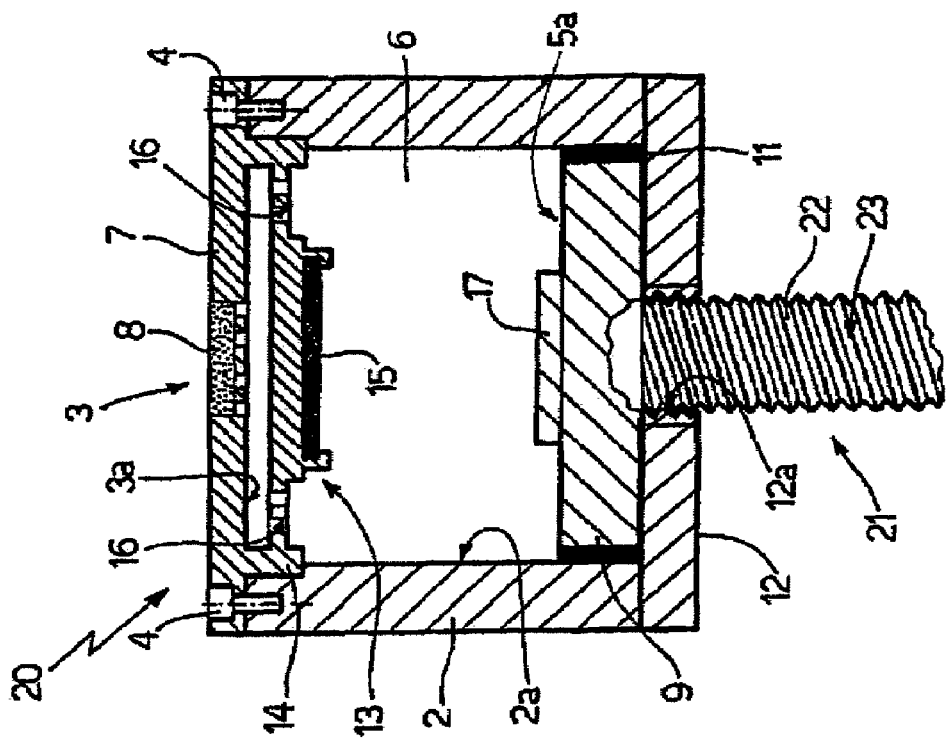
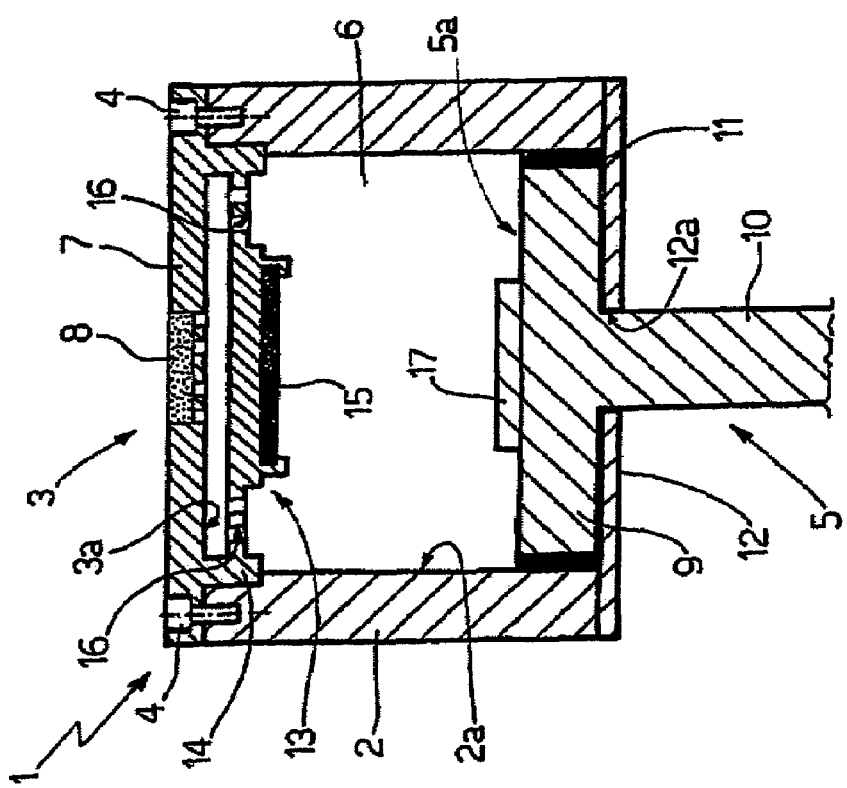
Fig.1
Fig.2

GASEOUS PRODUCT DETECTING DEVICE

TECHNICAL FIELD

The present invention relates to a gaseous product detecting device.

More specifically, the present invention relates to a detecting device for detecting radioactive gaseous products, such as radon, to which the following description refers purely by way of example.

BACKGROUND ART

The harmful effects on the human body of certain radioactive and non-radioactive gaseous substances has long been known. Moreover, many of these substances, existing underground, have been found to be present, not only in environments in which they are handled, but also in ordinary everyday living environments. All of which has led to a demand for more stringent monitoring of such substances, for the purpose of both research and prevention.

At international level, regulations governing the prevention and control of exposure to harmful radioactive and non-radioactive substances are currently in force, pursuant to regulations and directives issued by major national and international authorities (e.g. the International Committee for Radiation Protection (ICRP), the Environment Protection Agency (EPA) in America, and EU Directives covering all member countries).

In this connection, regulations recently issued in Italy governing radiation protection (Acts 241/2000 and 257/2001, pursuant to respective EU Directives) call for compulsory control of exposure to radon in working environments, and also provide for stricter monitoring and protocols.

The most commonly used measuring method is based on passive integrating trace detectors, which monitor the average radon concentration in inhaled air. This quantity is directly related to exposure, which is defined as the product of average concentration and the length of stay in the environment in which the detectors are installed. Using appropriate conversion coefficients, internal exposure of the respiratory system can then be determined.

Known radon detecting devices normally comprise a measuring cell of a few tens cc in volume; a filtering device, which allows radon into the measuring cell and retains the particulate present in the air; and a track detector housed inside the measuring cell, and which registers the alpha particles emitted by the radon and its decay products. A characteristic common to all these devices is that of having a constant-volume measuring cell.

Detecting devices of the above type are installed in the environment for an appropriate length of time, during which, radon penetrates by diffusion through the filtering device, and is detected by the detector as described above.

A major drawback of devices of this type lies in the measuring cell being brought into equilibrium with the outside environment as regards radon concentration (so-called initial transient) and being emptied of radon (so-called tail effect) within a given time period, which varies depending on the characteristics of the filtering device.

Another drawback lies in the detector not being protected, and so being subjected to continuous radiation, i.e. with no possibility of limiting its detection action to predetermined times and/or locations.

Both these drawbacks combined obviously have a negative effect on monitoring accuracy, by the detector being irradiated both before and after the correct monitoring time, thus supplying false radon concentration and exposure values.

That is, errors may be produced by irradiation caused by radon decay during the initial transient and during the tail effect when monitoring or calibrating in controlled atmospheres, or by decay of atmospheric radon entering the device during transport and storage.

To at least partly eliminate the above drawbacks, devices have been devised comprising mechanical shutters for protecting the detector.

Such solutions are often complex, are not particularly effective, and at best only act as safeguards during transport and storage of the device, leaving the initial transient and tail effect problems unsolved.

DISCLOSURE OF INVENTION

The present invention provides a gaseous product detecting device designed to eliminate the drawbacks of the known art in a straightforward, low-cost manner.

According to the present invention, there is provided a gaseous product detecting device having at least one measuring cell, and comprising at least one filtering element for retaining particulate present in the air entering said measuring cell, and at least one detecting element housed inside said measuring cell; said device being characterized by comprising a movable wall of said measuring cell; said movable wall being movable in a fluidtight manner between a withdrawn position, in which said measuring cell has a maximum volume, and a forward position, in which said measuring cell has a minimum volume and said detecting element is prevented from being impressed by resting against a shutter surface of said measuring cell.

In a preferred embodiment of the present invention, in the forward position of the movable wall, the detecting element rests against the movable wall itself.

BRIEF DESCRIPTION OF THE DRAWINGS

A number of non-limiting embodiments of the present invention will be described by way of example with reference to the accompanying drawings, in which:

FIG. 1 shows a longitudinal section, with parts removed for clarity, of a first embodiment of the device according to the present invention;

FIG. 2 shows a longitudinal section, with parts removed for clarity, of a second embodiment of the device according to the present invention;

DETAILED DESCRIPTION OF EMBODIMENTS OF THE INVENTION

Figure 3:
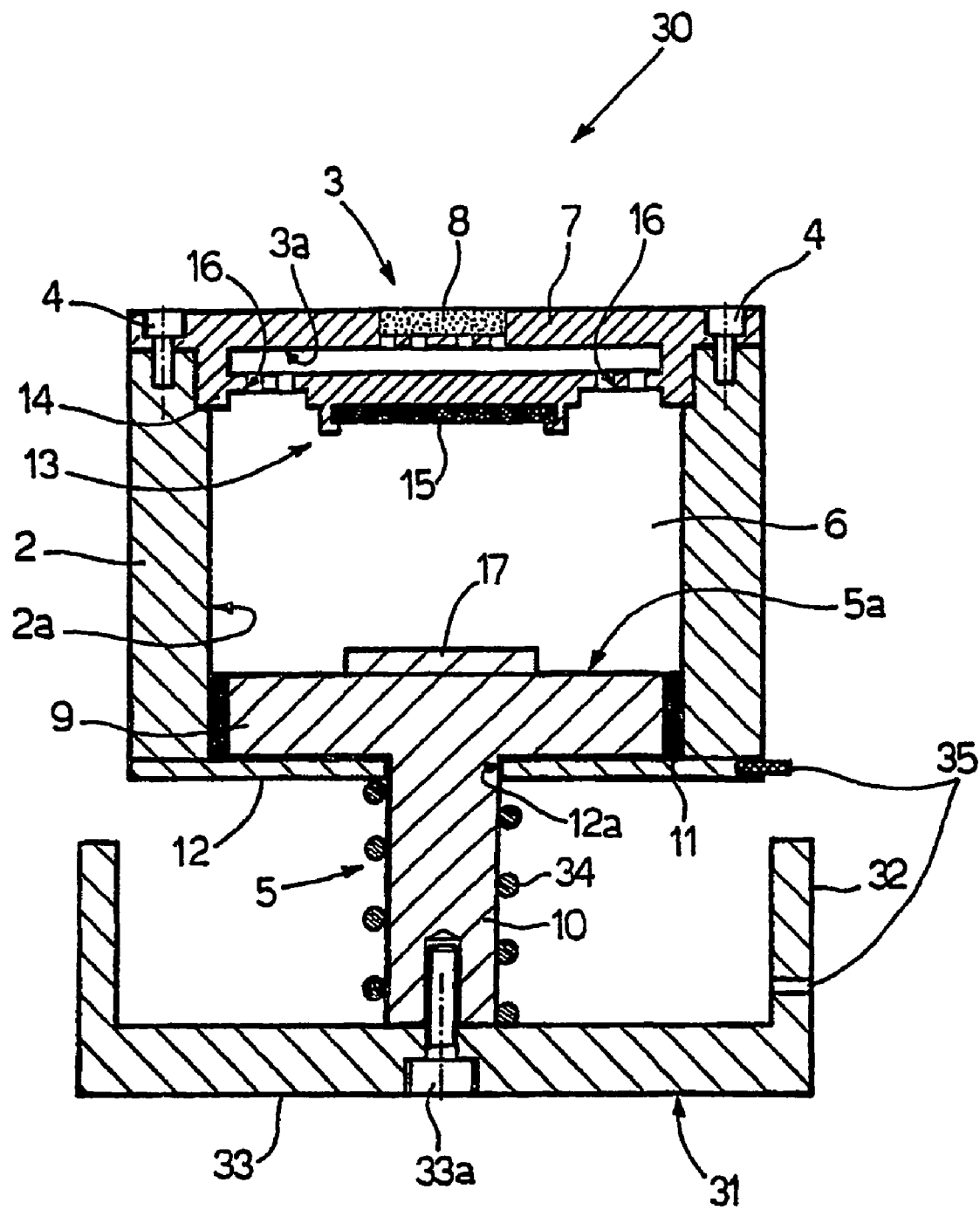
FIG. 3 shows a longitudinal section of a third embodiment of the device according to the present invention.

Number 1 in FIG. 1 indicates as a whole a gaseous product detecting device. Device 1 comprises a cylindrical wall 2; a circular filtering element 3 closing cylindrical wall 2 and fixed to it by screws 4; a piston 5 housed partly inside cylindrical wall 2, at the opposite end to filtering element 3, and sliding axially in a fluidtight manner inside cylindrical wall 2; and a measuring cell 6 defined by an inner surface 2a of cylindrical wall 2, by a surface 3a of filtering element 3 facing piston 5, and by a surface 5a of piston 5 facing filtering element 3.

Filtering element 3 comprises an annular support 7 fixed to cylindrical wall 2 by screws 4, and a known filter 8 (not described in detail) housed and fixed in known manner in the center of support 7.

Piston 5 comprises a cylindrical head 9 housed inside cylindrical wall 2 and defining one wall of measuring cell 6; and a rod 10 which, depending on the position of piston 5, is either completely outside or partly inside cylindrical wall 2. Head 9 is fitted laterally with a cylindrical seal 11 contacting inner surface 2a to ensure a fluidtight slide of piston 5.

Detecting device 1 comprises a ring 12 fixed to the opposite end of cylindrical wall 2 to that fixed with filtering element 3, and having a hole 12a sized to permit passage of rod 10 but not head 9 of piston 5, so as to permit movement of the piston while preventing detachment of the head from cylindrical wall 2.

Detecting device 1 also comprises a detecting element 13 housed inside measuring cell 6, close to filtering element 3. Detecting element 13 comprises a circular support 14 fixed in known manner to cylindrical wall 2; and known detector 15 (e.g. made of CR9, cellulose nitrate or polycarbonate) not described in detail, fixed to circular support 14 in a known manner, and facing piston 5. A peripheral portion of circular support 14 has a number of holes 16 (only four shown in FIG. 1) arranged in a circle and permitting passage of the air filtered by filter 8.

Piston 5 may assume a withdrawn position (FIG. 1) in which head 9 rests on ring 12 and measuring cell 6 has a maximum volume, and a forward position in which measuring cell 6 has a minimum volume and surface 5a rests against detector 15. More specifically, surface 5a is fitted with a shutter disk 17 projecting with respect to surface 5a and of the same dimensions as detector 15, so as to more effectively shield and prevent impression of detector 15.

In actual use, starting with piston 5 in the forward position, device 1 is immersed in the environment for monitoring, and piston 5 is moved into the withdrawn position. This movement produces a pumping effect, which sucks air through filter 8, so that measuring cell 6 fills rapidly, and is soon brought into equilibrium with the outside environment as regards radon concentration, thus solving the initial transient problems mentioned. When monitoring is to be interrupted, the piston is moved into the forward position, thus rapidly emptying measuring cell 6 and, at the same time, shielding detector 15 and so solving the tail effect problems mentioned.

Numbers 20 and 30 in FIGS. 2 and 3 indicate a further two embodiments of the detecting device according to the present invention, any parts of which identical with those of detecting device 1 are indicated using the same reference numbers as in FIG. 1, with no further description.

As shown in FIG. 2, detecting device 20 comprises a piston 21, in turn comprising a head 9, and a rod 22 having a threaded outer surface 23, so that piston 21 is moved by rotating rod 22.

As shown in FIG. 3, detecting device 30 comprises a cup-shaped body 31, in turn comprising a cylindrical wall 32 with an inside diameter larger than the outside diameter of cylindrical wall 2, and a circular wall 33 closing cylindrical wall 32. Cup-shaped body 31 is fixed by a screw 33a to the free end of rod 10 of piston 5, so that the concavity of cup-shaped body 31 faces piston 5. Detecting device 30 also comprises a spring 34 surrounding rod 10 and compressed between circular wall 33 of cup-shaped body 31 and ring 12.

Piston 5 of detecting device 30 is moved from the withdrawn position to the forward position by pressing circular wall 33 of cup-shaped body 31, and is kept in the forward position by known retaining means shown schematically and indicated 35. Piston 5 is restored to the withdrawn position by simply pressing lightly on circular wall 33, so that, once retaining means 35 are released, piston 5 is pushed into the withdrawn position by spring 34.

As will be clear from the foregoing description, the detecting device according to the present invention provides for bringing the measuring cell rapidly into equilibrium with the outside environment, thus solving initial transient problems, and, once monitoring is completed, provides for emptying the measuring cell rapidly, thus solving tail effect problems. This advantage is particularly important when calibrating the device immersed in a controlled-atmosphere chamber, in which case, improper calibration will impair the entire working life of the device. It is not surprising, therefore, that the strictest regulations relate to device calibration standards.

Moreover, the detecting device being activated and deactivated by a piston means that, once the standard values of the reference chamber in which the device is immersed are reached during calibration, the device can be activated from outside the reference chamber without disturbing the standard atmosphere of the reference chamber.

Figure 4:
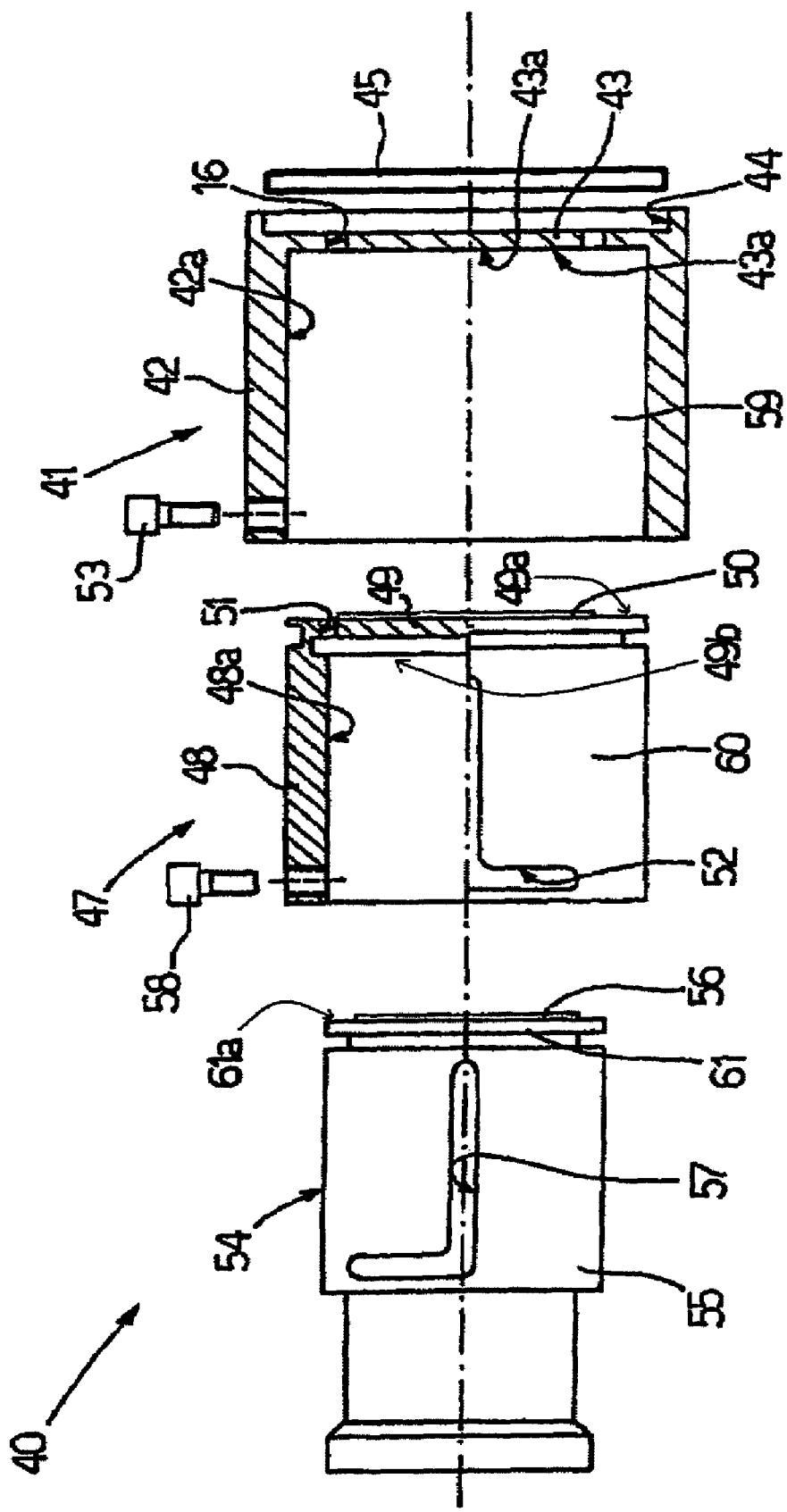
FIG. 4 shows an exploded view of a fourth embodiment of the device according to the present invention.

Number 40 in FIG. 4 indicates as a whole a fourth embodiment of the detecting device according to the present invention.

Detecting device 40 comprises a cup-shaped body 41, in turn comprising a cylindrical wall 42, and a circular wall 43 closing cylindrical wall 42. In circular wall 43 are formed a seat 44 for a filtering element 45 outside cylindrical wall 42, and a number of holes 16 allowing the air filtered by filtering element 45 to flow inside cylindrical wall 42. Device 40 also comprises a second cup-shaped body 47 which slides in a fluidtight manner inside first cup-shaped body 41, with its concavity facing outwards of cup-shaped body 41. Cup-shaped body 47 comprises a cylindrical wall 48; and a circular wall 49 closing cylindrical wall 48 and fitted with a detecting element 50 facing outwards of cylindrical wall 48. Circular wall 49 has a number of holes 51 allowing the filtered air to flow inside cylindrical wall 48.

Cylindrical wall 48 has an L-shaped slot 52, which is engaged by a pin 53 in cylindrical wall 42 of cup-shaped body 41 to guide and secure cup-shaped body 47 inside cup-shaped body 41.

Detecting device 40 comprises a piston 54, which slides in fluidtight manner inside cup-shaped body 47, and in turn comprises a substantially cylindrical body 55, and a detecting element 56 on the circular base 61 of cylindrical body 55 located, in use, inside cylindrical wall 48.

To guide and secure piston 54 inside cup-shaped body 47, cylindrical body 55 has an L-shaped slot 57 engaged by a pin 58 in cylindrical wall 48 of cup-shaped body 47.

In other words, detecting device 40 comprises a first measuring cell 59 defined by inner surfaces 42a and 43a of cup-shaped body 41, and by an outer surface 49a of circular wall 49; and a second measuring cell 60 defined by inner surfaces 48a and 49b of cup-shaped body 47, and by an outer surface 61a of circular base 61.

As will be clear from the foregoing description, detecting device 40 provides for eliminating the initial transient and tail effect drawbacks, by both measuring cells 59 and 60 being filled and emptied rapidly by the pumping effect produced by cup-shaped body 47 and piston 54, respectively. Moreover, detecting device 40 provides for shielding detecting elements 50 and 56, by their resting on circular walls 43 and 49, respectively.

Moreover, detecting device 40 has the added advantage of performing two monitoring operations simultaneously, with a considerable saving in space and, above all, cost, bearing in mind that, to be on the safe side, almost all monitoring operations are performed using at least two devices.

Figure 5:
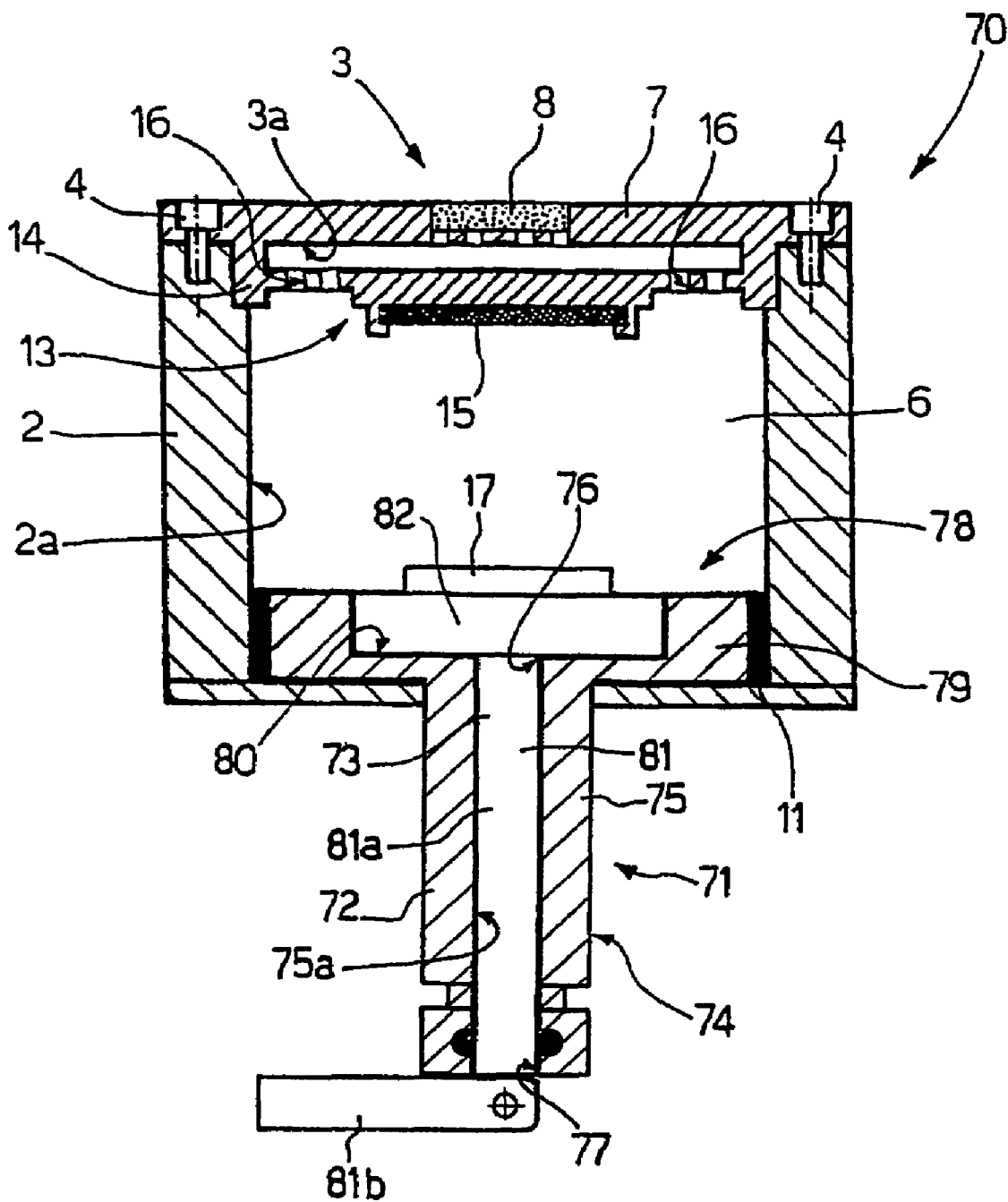
FIG. 5 shows a longitudinal section of a fifth embodiment of the device according to the present invention.

Number 70 in FIG. 5 indicates a further embodiment of the detecting device according to the present invention, any parts of which identical with those of detecting device 1 are indicated using the same reference numbers as in FIG. 1, with no further description.

As shown in FIG. 5, detecting device 70 comprises a piston 71, in turn comprising an outer portion 72, and an inner portion 73 which, according to a particular application of device 70, is free to move with respect to outer portion 72. Outer portion 72 comprises a tubular rod 74 defined by a hollow cylindrical wall 75 defining a cylindrical cavity 75a communicating with the outside through two circular openings 76 and 77 at respective ends of wall 75; and a head 78 comprising an annular wall 79, in the center of which is formed a dead circular cavity 80 facing detector 15 and having a central circular opening 76.

Inner portion 73 comprises a rod 81 which slides inside cylindrical cavity 75a; and a circular head 82 housed inside cavity 80 and having a surface 82a supporting shutter disk 17. More specifically, rod 81 comprises a front portion 81a, and a rear portion 81b hinged to front portion 81a, so that portions 81a and 81b can be positioned aligned with each other, or at a right-angle (as shown in FIG. 5).

As shown in FIG. 5, when portions 81a and 81b form a right-angle, inner portion 73 of piston 71 is locked with respect to, and moves integrally with, outer portion 72. More specifically, in this position, front portion 81a of rod 81 is housed entirely inside cavity 75a, and head 82 is housed in fixed manner inside cavity 80. Conversely, when portions 81a and 81b are aligned, rod 81 is free to slide inside cylindrical cavity 75a, so that inner portion 73 of piston 71 is no longer integral with outer portion 72, and can move head 82 to shield detector 15 by means of shutter disk 17. In other words, in this embodiment, the movable wall in the previous embodiments of the present invention comprises a peripheral portion defined by annular wall 79; and a central portion defined by head 82, which, according to a particular application of the device, is movable independently of the peripheral portion.

This affords the further advantage of enabling air to be pumped into measuring cell 6, to fill it with air for analysis, by means of outer portion 72 of piston 71, while detector 15 remains shielded by inner portion 73 of piston 71; and, once a condition of equilibrium is established between the radon and its decay products, impression of detector 15 is permitted by moving inner portion 73. This provides for even more accurate measurements, by only commencing the detection stage once equilibrium is established between the radon and its decay products.

In the embodiments described above, shutter disk 17 may itself define a detecting element, so that two readings can be taken in one measurement and in one measuring cell, while still maintaining the advantages of the pumping effect and shielding of the detecting elements.

Finally, the detecting device according to the present invention also has the major advantage of permitting effective overall monitoring on the basis of partial monitoring operations performed at different times, thus enabling accurate assessment of human exposure to gas in a given environment and over a given time period (e.g. a week, month, or year). In this case, the device is left in the monitored environment, and is activated when the subject comes in, and deactivated when the subject leaves. Alternatively, the device may be suitably adapted and worn as a personal dosimeter for monitoring inhaled air.

Clearly, changes may be made to the gaseous product detecting device according to the present invention without, however, departing from the scope of the accompanying claims.

For example, the detecting element may be located on a fixed wall of the measuring cell, where it is shielded by resting against the piston head, or it may be located on the piston head and shielded by resting against the fixed wall facing the piston. In particular, the filtering element may even define the fixed wall, against which the detecting element rests and is shielded.

Finally, the piston may be operated in any number of ways. For example, the piston of the detecting device featuring a spring about the piston rod may be operated electrically to perform automatic monitoring cycles.

What is claimed is:

1. A gaseous product detecting device for detecting an airborne substance present in an air flow into the device, the device having at least one measuring cell and comprising at least one filtering element for retaining particulate present in air entering said at least one measuring cell while permitting the substance to pass through the at least one filtering element for detection, and at least one detecting element housed inside said at least one measuring cell to detect levels of the substance having passed through the at least one filtering element, wherein said device comprises a wall formed as part of said at least one measuring cell, said wall movable in a fluidtight manner between a withdrawn position, in which said at least one measuring cell has a maximum volume, and a forward position, in which said at least one measuring cell has a minimum volume, movement between the forward and withdrawn positions producing a pumping effect which draws the airborne substance through the at least one filtering element and into the at least one measuring cell for detection, and wherein the at least one detecting element is prevented from being impressed by resting against a shutter surface of said at least one measuring cell.

2. The detecting device as claimed in claim 1, wherein said shutter surface rests against said at least one detecting element when said movable wall is in the forward position.

3. The detecting device as claimed in claim 2, wherein said movable wall comprises a peripheral portion, and a central portion inside said peripheral portion and movable independently of the peripheral portion, so as to separate a pumping operation from a shielding operation shielding said at least one detecting element.

4. The detecting device as claimed in claim 3, wherein said peripheral portion and said central portion are carried by a first rod and a second rod, respectively, said second rod being housed inside said first rod.

5. The detecting device as claimed in claim 1, wherein said at least one detecting element is fixed to said movable wall.

6. The detecting device as claimed in claim 1, comprising a piston member carrying said movable wall.

7. The detecting device as claimed in claim 6, comprising a cylindrical wall closed at one end by said at least one filtering element, and in which said piston member slides in a fluidtight manner, said cylindrical wall defining said at least one measuring cell together with said at least one filtering element and said movable wall.

8. The detecting device as claimed in claim 6, wherein said piston member comprises a rod having a threaded outer surface.

9. The detecting device as claimed in claim 6, comprising a spring surrounding a rod of said piston member, and retaining means for retaining said movable wall in the forward position; said spring being compressed when said movable wall is in the forward position, so as to force said movable wall into the withdrawn position.

10. The detecting device as claimed in claim 6, wherein said piston member comprises an inner cavity defining a further measuring cell together with a surface of a further movable wall which slides in a fluidtight manner inside said cavity, said further measuring cell communicating with said at least one measuring cell, and a further detecting element being located inside said further measuring cell.

11. The detecting device as claimed in claim 10, comprising a further piston member carrying said further movable wall.

12. The detecting device as claimed in claim 10, wherein said further detecting element is fixed to said further movable wall.

* * * * *